United States Patent
Griffin et al.

(10) Patent No.: US 10,596,106 B2
(45) Date of Patent: Mar. 24, 2020

(54) COMPOSITIONS AND METHODS FOR CERUMEN REMOVAL

(71) Applicant: Eosera Inc., Fort Worth, TX (US)

(72) Inventors: Joe Griffin, Burleson, TX (US); Eric Anderson, Southlake, TX (US)

(73) Assignee: Eosera, Inc., Fort Worth, TX (US)

( * ) Notice: Subject to any disclaimer, the term of this patent is extended or adjusted under 35 U.S.C. 154(b) by 0 days.

(21) Appl. No.: 16/325,284

(22) PCT Filed: Aug. 9, 2017

(86) PCT No.: PCT/US2017/046121
§ 371 (c)(1),
(2) Date: Feb. 13, 2019

(87) PCT Pub. No.: WO2018/034910
PCT Pub. Date: Feb. 22, 2018

(65) Prior Publication Data
US 2019/0201330 A1 Jul. 4, 2019

Related U.S. Application Data

(60) Provisional application No. 62/374,888, filed on Aug. 14, 2016.

(51) Int. Cl.

| | | |
|---|---|---|
| *A61K 9/00* | (2006.01) | |
| *A61K 47/02* | (2006.01) | |
| *A61K 31/225* | (2006.01) | |
| *A61K 31/19* | (2006.01) | |
| *A61K 31/194* | (2006.01) | |
| *A61P 27/16* | (2006.01) | |
| *A61K 31/191* | (2006.01) | |
| *A61K 45/06* | (2006.01) | |

(52) U.S. Cl.
CPC ............ *A61K 9/0046* (2013.01); *A61K 31/19* (2013.01); *A61K 31/191* (2013.01); *A61K 31/194* (2013.01); *A61K 31/225* (2013.01); *A61K 45/06* (2013.01); *A61K 47/02* (2013.01); *A61P 27/16* (2018.01)

(58) Field of Classification Search
None
See application file for complete search history.

(56) References Cited

U.S. PATENT DOCUMENTS 4,105,783 A * 8/1978 Yu ...................... A61K 9/0014
514/459

FOREIGN PATENT DOCUMENTS

| WO | WO 2011/085155 | * | 7/2011 |
| WO | WO 2011/085155 A2 | | 7/2011 |

OTHER PUBLICATIONS

Glycozoo Dermatology, Dermazoo, Sep. 28, 2013.
Fullington et al., Evaluation of the safety and efficacy of a novel product for the removal of impacted human cerumen, BMC Ear, Nose and Throat Disorders, vol. 17, Issue 5, Jun. 2, 2017.
Knebl et al., In vitro comparison of three earwax removal formulations for the disintegration of earwax, F1000 Research, vol. 5:2784, Nov. 29, 2016.
PCT Search Report and Written Opinion, dated Oct. 27, 2017.

* cited by examiner

*Primary Examiner* — Dennis Heyer
(74) *Attorney, Agent, or Firm* — Kirby Drake

(57) ABSTRACT

Systems and methods for removal of human cerumen are provided. A composition for removal of cerumen includes at least one cerumenolytically acceptable active agent and an otologically acceptable vehicle. The cerumenolytically acceptable active agent may be an alpha-hydroxy acid (AHA). Exemplary AHA may include, but are not limited to, glycolic acid, tartronic acid, lactic acid, malic acid and any derivative or mixture thereof. The otologically acceptable vehicle may be sodium or potassium salts of bicarbonate aqueous buffer. Yet further, the otologically acceptable vehicle may contain sodium docusate. Cerumen may be removed and/or a cerumen impaction may be treated by administering to a patient in need thereof a composition comprising an AHA and an otologically acceptable vehicle.

18 Claims, No Drawings

COMPOSITIONS AND METHODS FOR CERUMEN REMOVAL

CROSS REFERENCE TO RELATED APPLICATION

This application claims the benefit under 35 U.S.C. § 119(e) of U.S. Provisional Patent Application Ser. No. 62/374,888 filed on Aug. 14, 2016, entitled "Novel Compositions and Methods for Cerumen Removal," which is incorporated by reference in its entirety.

FIELD OF THE DISCLOSURE

The present disclosure generally pertains to the removal of human cerumen. More particularly, but not by way of limitation, the present disclosure is directed to advantageous compositions for assisting in the removal of human cerumen.

BACKGROUND

Cerumen or earwax is composed of desquamated sheets of corneocytes originating from the deep and superficial external auditory canal, mixed with glandular secretions. These glandular secretions originate in the sebaceous and ceruminous glands in the auditory canal secrete lipids and peptides, respectively, into the cerumen. Hairs in the external third of the canal also produce glandular secretions that contribute to cerumen's composition. Cerumen forms a protective layer on the skin of the external ear canal. The consistency of, and thus the difficulty in removing, cerumen varies from individual to individual and is at least partially genetically determined.

Cerumen build-up and impaction in the external ear canal is a significant problem, especially for the infant and geriatric populations of the world. In the United States, about 8 million cerumen removals take place each year, and in the United Kingdom, the number is 2 million. Individuals possessing hairy ear canals, narrow ear canals, or osteoma are more disposed to such build-up or impaction. In addition, some literature suggests that the use of cotton buds to clean the external ear canal interferes with the body's normal shedding of earwax and epithelium and increases the chance of such build-up and impaction. Build-up and/or impaction of earwax may cause irritation, itching, pain, infection, or conductive hearing loss. Wax removal is necessary to alleviate these conditions. Cerumen removal is also required when it is necessary to examine the tympanic membrane. The process of removing impacted cerumen is tedious and time consuming for health care providers and is often painful for the patient.

Various compositions for allegedly softening or removing human cerumen are known. Several commercial products contain carbamide peroxide (6.5%) in an anhydrous glycerin vehicle as defined in the FDA monograph 21 CFR part 344. Examples of these products are Debrox® Earwax Removal Aid, Murine® Ear Wax Removal Drops, and Flents® Earwax Removal Aid. Another product is Cerumenex® Eardrops, a prescription product containing triethanolamine polypeptide oleate-condensate (10%). Cerumenex® sometimes resulted in irritation of the ear canal, and its distribution was discontinued in 2002 in the United States.

In addition, other agents have been somewhat effective in softening earwax. Such agents include glycerin (glycerol), olive oil, almond oil, mineral oil, sodium carbonate, sodium bicarbonate, hydrogen peroxide, docusate sodium, and dichlorobenzene. After softening with one of these agents, irrigation with body temperature water or saline is often performed to remove the softened cerumen. However, there is literature that reports that Cerumenex® Eardrops and Murine® Ear Drops were no more effective that placebo (saline) in a randomized, controlled clinical evaluation.

Compositions that may facilitate the removal of earwax have also been the subject of several patents and patent applications. For example, U.S. Pat. No. 4,895,875 (Winston) discloses stabilized peroxide solutions comprising urea peroxide and glycerin and methods of preparation and uses for cerumen removal; U.S. Pat. No. 5,296,472 (Sanchez et al.) discloses compositions comprising cyclodextrins and methods of use for cerumen removal; and U.S. Pat. No. 5,480,658 (Melman) discloses compositions comprising acetic acid and boric acid in a water base useful for cleaning the external ear canal of pets. Patent application US2004/0126436 (Cagle et al.) proposes a cerumenolytic composition utilizing a methyl trypsin protease enzyme to assist in the removal of human cerumen from the external ear canal. And patent application WO2011085155A2 (Shapiro et al.) describes a product consisting of bile salts, limonene, and sodium bicarbonate for the dissolution and removal of human cerumen.

Yet another cerumenolytic product is an aqueous solution of sodium bicarbonate, which has been prepared by physicians and used to treat impacted cerumen. If this solution is used, physicians are inconvenienced by having to prepare the solution for each individual patient.

SUMMARY

Embodiments of the present disclosure may provide a composition comprising a formulation for the removal of cerumen comprising at least one cerumenolytically acceptable active agent and an otologically acceptable vehicle. The cerumenolytically acceptable active agent may be an alpha-hydroxy acid (AHA). Exemplary AHA may include, but are not limited to, glycolic acid, tartronic acid, lactic acid, malic acid and any derivative or mixture thereof. The otologically acceptable vehicle may be sodium or potassium salts of bicarbonate aqueous buffer. Yet further, the otologically acceptable vehicle may contain sodium docusate. Another embodiment of the present disclosure may provide a method for removing cerumen comprising administering to a patient in need thereof a composition comprising an AHA and an otologically acceptable vehicle. Still further, another embodiment of the present disclosure may provide a method of treating a patient having cerumen impaction by administering a composition comprising an AHA and an ontologically acceptable vehicle.

Embodiments of the present disclosure may further provide a composition for the removal of cerumen comprising: at least one cerumenolytically acceptable active agent; and an otologically acceptable vehicle. The cerumenolytically acceptable active agent may be an alpha-hydroxy acid (AHA). The AHA may be selected from the group comprising: glycolic acid, tartronic acid, lactic acid, malic acid or a combination thereof. The AHA may comprise about 1-30% of the composition, or about 1-10% of the composition. The otologically acceptable vehicle may be a sodium or potassium salts of bicarbonate aqueous buffer. The otologically acceptable vehicle further may include sodium docusate. The composition may be a topical composition administered to the ear canal.

Further embodiments of the present disclosure may provide a method for removing cerumen from a patient in need thereof comprising: administering to a patient in need thereof a composition comprising an AHA and an otologically acceptable vehicle. The composition may be administered topically. The composition may remain in contact with the cerumen for about 15-30 minutes prior to removal. The composition may be applied and removed at least once. The composition may result in about 65% change in cerumen.

Additional embodiments of the present disclosure may provide a method of treating a cerumen impaction comprising: administering topically to a patient's ear in need thereof a composition having an AHA and an otologically acceptable vehicle. The composition may improve cerumen impaction comprising full occlusion, crescent shape, or ring shape by alleviating at least one or more blockage symptoms selected from the group consisting of: hearing loss, fullness feeling, ear ringing, ear itching, water trapping, ear pain, ear irritation or a combination thereof. The composition may be administered unilaterally or bilaterally. The composition may reduce cerumen impaction to less than about 3%. The composition may reduce cerumen impaction from about 76-100% to at least about 3-75%, from about 51-75% to at least about 3-50%, or from about 26-50% to at least about 3-35%.

Other technical features may be readily apparent to one skilled in the art from the following figures, descriptions and claims.

DETAILED DESCRIPTION

A need exists for an improved product for the breakdown and removal of human cerumen that is more efficacious and that does not suffer from the limitations of currently available cerumenolytics. Embodiments of the present disclosure provide beneficial compositions and methods to fill this need.

I. Cerumenolytic Compositions

A major component of cerumen is the desquamated skin cells (keratinocytes) that combine with the secreted lipids and peptides. Therefore, embodiments of the present disclosure may provide a composition designed to safely break down the individual components to allow for easy removal of the cerumen. Compositions according to embodiments of the present disclosure may comprise a cerumenolytically acceptable component. Yet further, the composition can comprise at least one or more cerumenolytically acceptable components or combinations or mixtures thereof.

As used herein, "cerumenolytically acceptable component" is an agent that alone or in combination degrades, destroys, reduces or otherwise diminishes the amount of cerumen in the ear of a patient. One class of cerumenolytically acceptable components is the alpha-hydroxy acids. An alpha-hydroxy acid (AHA) of alpha-carbon chain lengths from 0 to 16, based on the ability of it to react with to weaken the intra-lipid binding properties of the lipids that hold dead skin cells together, may be utilized in the compositions and methods of the present disclosure to disrupt the desquamated cells contained within cerumen. For purposes of this specification, AHA will satisfy the foregoing requirements referred to as being "cerumenolytically acceptable." This ingredient may comprise a liquid composition or a solid composition, such as a lyophilized powder or solid tablet.

Exemplary AHAs may include, but are not limited to, lactic acid, malic acid, citric acid, 2-hydroxybutanoic acid, mandelic acid, gluconic acid, glycolic acid (i.e., alpha-hydroxyethanoic acid), tartaric acid, ascorbic acid, alpha-hydroxyoctanoic acid, alpha-hydroxycaprylic acid, and salicylic acid, as well as derivatives thereof (e.g., compounds substituted with hydroxyls, phenyl groups, hydroxyphenyl groups, alkyl groups, halogens, as well as combinations thereof). Preferred AHAs may include glycolic acid, lactic acid, malic acid, and tartronic acid. These acids may be in D, L, or DL form and may be present as free acid, lactone, or partial salts thereof. All such forms are encompassed by the term "acid." Preferably, the acids are present in the free acid form. In certain preferred embodiments, the AHAs useful in the compositions described herein may be selected from the group consisting of glycolic acid, lactic acid, malic acid, tartronic acid, and mixtures thereof.

In one embodiment of the present disclosure, the concentration of AHA may be from about 0.1-50%, alternatively from about 0.1-1%, about 0.5-1%, 1.0-1.5%, about 1.5-3%, about 3%-5%, about 5%-10%, about 5-30%, about 10-30%, about 15-30%, or any range derivable therein. In further embodiments, the concentration may be about 1-10%.

As used herein, the term "otologically acceptable vehicle" refers to any substance or combination of substances that may act as a carrier for an active agent or agents and that are suitable for administration to the external ear canal. By way of example, an otologically acceptable vehicle may comprise any combination of preservatives, surfactants, viscosity enhancers, penetration enhancers, buffers, sodium chloride, sodium docusate or other salts, solubilizers, stabilizers, pH adjusters, tonicity agents, fillers, demulcents, and water. The otologically acceptable vehicle for the compositions of the present disclosure may preferably be an aqueous vehicle.

In one embodiment of the present disclosure, the composition may contain an alpha-hydroxy acid (such as glycolic acid) or its salt in a stable and otologically acceptable vehicle.

II. Treatment or Removal of Cerumen

In accordance with the present disclosure, the composition provided in any of the above-described pharmaceutical carriers may be administered to a subject who has or is at risk of developing cerumen build-up. Risk factors may include, but are not limited to hairy ear canals, narrow ear canals, or osteoma. One of skill in the art can determine the patients who would potentially benefit from a therapeutic agent that would reduce cerumen build-up.

Yet further, the composition provided herein may be administered to a subject at risk or a subject that has a cerumen impaction. Administration of the composition thereby may treat or alleviate the cerumen impaction. Cerumen impaction is defined by accumulation of cerumen that causes symptoms, and/or prevents assessment of the ear canal/tympanic membrane, or audiovestibular system or both. Thus, treatment of cerumen impaction may result in improvements of at least one or more blockage symptoms.

Other such uses for the present composition may be, for example, given the presence of a tympanostomy tube or other rupture or hole in the tympanic membrane, the compositions of the present disclosure may be used to cleanse the middle and external ear of the viscous exudate that often results from a middle ear infection. This viscous exudate can include conditions such as secretory otitis media, mucoid otitis media, serous otitis media, and chronic otitis media with effusion. These conditions sometimes lead to hearing loss via inflammation and/or the inhibition of ossicular sound conduction.

Once prepared, the cerumenolytically active compositions as described herein may be placed into the ear of a patient in need thereof. By "placing in the ear," the composition can be applied to the ear such that the wax is in contact with the cerumenolytically active composition. This may be performed by dropping a liquid in the ear. Alternatively, this may be achieved by a delivery device like a syringe or other otologically appropriate delivery devices.

Once applied to the ear the composition may remain in contact with the cerumen for a period ranging from a few to many minutes. In one embodiment of the present disclosure, the contact time may be from approximately 1-60 minutes, alternatively from approximately 5-45 minutes, or alternatively from approximately 15-30 minutes or any range derivable therein. The composition can be administered unilaterally and/or bilaterally as necessary.

Accordingly, the present disclosure may provide a method for removing cerumen from the ear of a patient in need thereof. The method may include applying a cerumenolytically active composition to the wax in the ear of the patient, waiting an appropriate length of time, and then rinsing the degraded cerumen out of the ear with an otologically appropriate rinse or water, or saline. Multiple applications of the cerumenolytically active composition may be useful. For instance, the composition may be applied multiple times per day as necessary. Alternatively, it may be applied once daily, every other day, once a week, once a month and the like.

Applications of the cerumenolytically active composition may result in improvement in blockage symptoms, and more specifically, may result in a percentage change in cerumen or ear wax. Such a percentage change can include a weighted average percentage change in earwax or cerumen over the treatment period, including, but not limiting to about 50% change, about 55% change, about 60% change, about 65% change, about 70% change, about 75% change, about 80% change, about 85% change, about 90% change, about 95% change and/or about 100% change.

For purposes of the present disclosure, beneficial or desired clinical results include, but are not limited to, alleviation of symptoms, improvement of symptoms, diminishment of extent of cerumen build-up, whether objective or subjective. The improvement may be any observable or measurable improvement in earwax blockage symptoms or cerumen impaction. Thus, one of skill in the art may realize that a treatment may improve the patient condition, but may not be a complete cure of the condition. Earwax blockage symptoms and/or cerumen impaction can comprise, but are not limited to, decreased hearing, feeling of fullness, ringing or noises in the ear, water trapping or cracking noise after swimming or shower, ear irritation/discomfort, earache or tingling or pain.

Exemplary improvements in blockage symptoms may comprise, but are not limited to, an improvement or decrease in fullness of affected ears, a decrease in ear itching, a decrease in water trapping or cracking, decrease in ringing or noises in the ear (tinnitus), decrease in earache and/or ear pain, and/or an increase in hearing. Yet further, improvements may also include, a decrease in dizziness and/or overall improvement of quality of life. Further improvements can also comprise a decrease in ear irritation or discomfort. Still further improvements include better visualization of the ear canal and tympanic membrane, including but not limited to totally dissolved as defined by earwax impaction reduced to less than about 3% or partially dissolved as defined by earwax impaction reduced by at least one of the following scales, i.e., from about 76-100% to at least about 3-75%, or from about 51-75% to at least about 3-50%, from about 26-50% to at least about 3-35% and/or any derivable range therein.

While the compositions and methods of the present disclosure have been described in terms of preferred embodiments, it will be apparent to those of skill in the art that variations may be applied to the compositions and/or methods and in the steps or in the sequence of steps of the method described herein without departing from the concept, spirit and scope of the present disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present disclosure.

III. Examples

The following examples are included to demonstrate preferred embodiments of the present disclosure. It should be appreciated by those of skill in the art that the techniques disclosed in the examples which follow representative techniques discovered by the inventor to function well in the practice of the present disclosure, and thus can be considered to constitute preferred modes for its practice. However, those of skill in the art should, considering the present disclosure, appreciate that many changes can be made in the specific embodiments which are disclosed and still obtain a like or similar result without departing from the spirit and scope of the present disclosure.

Example 1

In Vitro Efficacy Testing on Artificial Cerumen

Due to the challenges in obtaining consistently sufficient quantities of human cerumen, an artificial cerumen was used initially. The artificial cerumen consisted of a mixture of three components. The first component (30-50%) is a lipid mixture based upon the reported composition of the lipids in earwax. The second component (30-40%) is homogenized mammalian skin cells, which simulates the desquamated epidermal cells in earwax. The third component (10-20%) is lyophilized bovine serum, which simulates the other components of earwax that are secreted from the ceruminous and sebaceous glands.

Approximately equal samples of the artificial cerumen were rolled into small balls (~30 mg) and placed into 13×100 mm borosilicate glass test tubes. The artificial cerumen samples were pre-warmed in an oven at approximately 37 degrees C. to simulate the body temperature of the ear canal. The artificial cerumen samples were removed from the oven, and a volume of the formulation solution (0.8 mL) was added to each of the test tubes to completely cover the artificial cerumen samples. Debrox® was also added to two separate samples of the artificial cerumen, to serve as a comparison. The samples and solutions were then heated in an oven at approximately 37 degrees C. for a total of 30 minutes, and the samples were removed from the oven at 5-minute, 10-minute, 15-minute, and 30-minute time points to observe and score the breakdown of the artificial cerumen samples.

A scoring system from 0 to 4 was developed for qualifying the breakdown of the artificial cerumen samples. A 0-score represented no change in the sample, and a 4-score represented complete breakdown of the sample into very small fragments. All samples were scored at 5-minute, 10-minute, 15-minute, and 30-minute time points. The scores for representative formulations and control formulations (either water or marketed comparator) are summarized in the tables 1-3:

TABLE 1

Scores for Breakdown of Artificial Cerumen

| Solution | 5 min | 10 min | 15 min | 30 min |
|---|---|---|---|---|
| Formulation (1.0% Glycolic Acid) | 1, 2, 2, 3 | 3, 3, 3, 3 | 4, 4, 3, 4 | 4, 4, 4, 4 |
| Debrox ® | 0, 0 | 0, 0 | 0, 0 | 0, 0 |

Summary of a representative experiment with a test formulation containing 1.0% glycolic acid in an otologically acceptable buffer compared to a currently marketed product.

TABLE 2

Scores for Breakdown of Artificial Cerumen

| Solution | 5 min | 15 min | 30 min |
|---|---|---|---|
| Formulation (10.0% Tartronic acid) | 1.03 (n = 15) | 3.17 (n = 15) | 3.90 (n = 15) |
| Water | 1.0 (n = 18) | 1.0 (n = 18) | 1.0 (n = 18) |

Summary of a series of experiments with a test formulation containing 10.0% Tartronic acid in an otologically acceptable buffer compared to water. The number in parenthesis corresponds to the number of replicates compared during these experiments.

TABLE 3

Scores for Breakdown of Artificial Cerumen

| Solution | 5 min | 15 min |
|---|---|---|
| Formulation (30.0% Lactic acid) | 3 | 3 |
| Formulation (30.0% Malic acid) | 2 | 3 to 4 |
| Water | NA | 1 |

Summary of an experiment with test formulations containing 30.0% of either Lactic acid or Malic acid in an otologically acceptable buffer compared to water. The wax breakdown score for the water at 5 minutes was inadvertently not recorded during the experiment Historically water has shown an average score of 1 at the 5-minute timepoint.

Example 2

In Vitro Efficacy Testing on Human Cerumen

Upon accumulating a sufficient supply of human cerumen samples, the product formulation was tested on human cerumen. Small, heterogeneous samples of cerumen were placed into 13×100 mm borosilicate glass test tubes. The cerumen samples were pre-warmed in an oven at approximately 37 degrees C. to simulate the body temperature of the ear canal. The cerumen samples were removed from the oven, and a volume (0.8 mL) of the formulation solution was added to each of the test tubes to completely cover the cerumen samples. Debrox® was also added to two separate samples of the artificial cerumen, to serve as a comparison. The samples and solutions were then heated in an oven at approximately 37 degrees C. for a total of 30 minutes, and the samples were removed from the oven at 5-minute, 10-minute, 15-minute, and 30-minute time points to observe and score the breakdown of the artificial cerumen samples.

The same visual scoring system from 0 to 4 was developed for qualifying the breakdown of the cerumen samples. All samples were scored at 5-minute, 10-minute, 15-minute, and 30-minute time points. The scores for a representative formulation and for Debrox® are summarized in Table 4.

TABLE 4

Breakdown Scores to Human Cerumen

| Solution | 5 min | 10 min | 15 min | 30 min |
|---|---|---|---|---|
| Formulation (1.0% Glycolic acid) | 0, 2, 0, 2 | 0, 3, 0, 4 | 2, 4, 2, 4 | 2, 4, 3, 4 |
| Debrox ® | 0, 0 | 0, 0 | 0, 0 | 0, 0 |

Summary of a representative experiment with a test, formulation containing 1.0% glycolic acid in an otologically acceptable buffer compared to a currently marketed product in human cerumen samples.

Example 3

Clinical Safety and Efficacy Evaluation in Humans with Excessive Cerumen

Utilizing an Institutional Review Board (IRB) approved human clinical study protocol, a candidate formulation was evaluated in vivo to determine safety and efficacy. Human subjects were recruited based specific inclusion criteria. The primary inclusion criteria were that the human subjects had to provide informed consent to participate in the trial and have at least 50% of the ear canal occluded by cerumen.

Otoscope examination revealed that 11 (58%) subjects had 51% or more impaction bilaterally and 8 (42%) subjects unilaterally. Twenty (67%) ears had severe blockage with 76-100% impactions and 10 (33%) had moderate blockage with 51-75% impactions (Table 5).

Full Occlusion was observed in 15 (50%) of the ears, Crescent shape in 10 (33%), and Ring shape in 5 (17%). Most them (24, 80%) appeared wet with normal consistency, and the rest were dry with normal appearance (4, 13%) or packed (2, 7%).

TABLE 5

Cerumen Evaluation

| Variable | # of Ears | Percent (%) |
|---|---|---|
| Ear Impaction | | |
| 51-75% | 10 | 33 |
| 76-100% | 20 | 67 |
| Shape | | |
| Full occlusion | 15 | 50 |
| Ring | 5 | 17 |
| Crescent | 10 | 33 |
| Appearance | | |
| Wet, normal | 24 | 80.00 |
| Wet, tarry | 0 | — |
| Wet, firm nuggets | 0 | — |
| Dry, normal | 4 | 13 |
| Dry, flakes | 0 | — |
| Dry, packed | 2 | 7 |
| Total | 30 | 100 |

The subjects that met the inclusion criteria were scheduled for a follow-up visit to receive treatment with the test formulation. The test formulation was instilled into the ear for 15 minutes. After 15 minutes, the formulation was drained from the ear and rinsed with warm water and then graded by a physician according to a scale approved in the study protocol. Following grading after the first treatment and rinse, subjects that did not have full clearance (wherein clearance is defined as being able to fully visualize the tympanic membrane (eardrum)), subjects were given a second treatment for 15 minutes. After rinsing following the second treatment, subjects were graded again.

The test formulation was deemed safe by the physician that conducted the study and the primary efficacy results are presented in Table 6.

TABLE 6

|  | Number of Ears | Percent (%) |
|---|---|---|
| Ear impaction before instillation |  |  |
| 51-75% | 12 | 40 |
| 76-100% | 18 | 60 |
| Ear impaction after first rinsing (n = 30) |  |  |
| Clear | 16 | 53.33 |
| Receiving second treatment | 14 | 46.67 |
| Ear impaction after second rinsing (n = 14) |  |  |
| Clear | 9 | 64.29 |
| Not clear | 5 | 35.71 |
| Summary of both treatments |  |  |
| Clear | 25 | 83.33 |
| Not clear | 5 | 16.67 |

As indicated in Tables 7 and 8, most of the ears/subjects that had earwax blockage symptoms experienced remarkable improvement with the treatment. Feeling of fullness disappeared in 92% of the affected ears; ears itching, 91%; water trapping or cracking, 78%, and, decreased hearing, 71%. After the treatment, a few subjects indicated that they had experienced "new" symptoms that they did not have prior to treatment such as feeling of fullness (n=3), ear irritation or discomfort (n=3).

TABLE 7

Improvement of Ear Specific Earwax Blockage Symptoms - per Ear Analysis

| Variable | Present at Baseline | Absent after Treatment |
|---|---|---|
| Decreased hearing [1] | 14 | 10 (71) |
| Feeling of fullness | 12 | 11 (92) |
| Ear itching | 11 | 10 (91) |
| Ringing or noises in the ear (tinnitus) [1] | 11 | 9 (82) |
| Water trapping or cracking noise after swimming or shower [1] | 9 | 7 (78) |
| Ear irritation/discomfort | 3 | 2 (67) |
| Earache, tingling or pain | 1 | 1 (100) |

[1] Post-treatment data was not available for one ear for each of these three symptoms.

TABLE 8

Ear Specific Ear Blockage Symptom Before and After Treatment - per Ear Analysis

|  | Post-Treatment | | | |
|---|---|---|---|---|
| Pre-Treatment | Yes | No | Total | p-value |
| Feeling of fullness |  |  |  |  |
| Yes | 1 (8%) | 11 (92) | 12 (43) | 0.0325 |
| No | 3 (19) | 13 (81) | 16 (57) |  |
|  | 4 (14) | 24 (86) | 28 (100) |  |
| Ear irritation/discomfort |  |  |  |  |
| Yes | 1 (33) | 2 (67) | 3 (11) | 0.6547 |
| No | 3 (12) | 22 (88) | 25 (89) |  |
|  | 4 (14) | 24 (86) | 28 (100) |  |
| Ear Itching |  |  |  |  |
| Yes | 1 (9) | 10 (91) | 11 (39) | 0.0209 |
| No | 2 (12) | 15 (88) | 17 (61) |  |
|  | 3 (11) | 25 (89) | 28 (100) |  |
| Earache, tingling or pain |  |  |  |  |
| Yes | 0 | 1 (100) | 1 (4) | 1.0000 |
| No | 1 (4) | 26 (96) | 27 (96) |  |
|  | 1 (4) | 27 (96) | 28 (100) |  |
| Ringing or noises in the ear tinnitus) |  |  |  |  |
| Yes | 2 (18) | 9 (82) | 11 (39) | 0.0027 |
| No | 0 | 17 (100) | 17 (61) |  |
|  | 2 (7) | 26 (93) | 28 (100) |  |
| Decreased hearing |  |  |  |  |
| Yes | 4 (29) | 10 (71) | 14 (50) | 0.0209 |
| No | 2 (14) | 12 (86) | 14 (50) |  |
|  | 6 (21) | 22 (79) | 28 (100) |  |
| Water trapping or cracking noise after swimming or shower |  |  |  |  |
| Yes | 2 (22) | 7 (78) | 9 (32) | 0.0956 |
| No | 2 (11) | 17 (89) | 19 (68) |  |
|  | 4 (14) | 24 (86) | 28 (100) |  |

1. p-values of McMemar's test for within-ear before-and-after comparison.

Two subjects had complained of dizziness at baseline, but the symptom disappeared after the treatment (Table 10). Six subjects indicated that earwax blockage had impacted their overall quality of life. Of them, 5 (83%) indicated such situation has improved with the treatment, while it still troubled one subject (Subject 119) who had severe occlusion that required physical removal with a curette. He had complained of discomfort in tympanic membrane after the treatment and was referred to an ENT by the Investigator.

TABLE 10

Improvement of Systematic Earwax Blockage Symptoms - per Subject Analysis

| Variable | Present at Baseline | Absent after Treatment |
|---|---|---|
| Dizziness | 2 | 2 (100) |
| Restlessness/anxiety | 0 | — |
| Impact on overall quality of life [1] | 6 | 5 (83) |

Total = 19 subjects.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A composition for the removal of cerumen comprising:
   at least one cerumenolytically acceptable active agent, wherein the cerumenolytically acceptable active agent is an alpha-hydroxy acid (AHA); and
   an otologically acceptable vehicle, wherein the otologically acceptable vehicle is a sodium or potassium salts of bicarbonate aqueous buffer.

2. The composition of claim 1, wherein the AHA is selected from the group comprising:
   glycolic acid, tartronic acid, lactic acid, malic acid or a combination thereof.

3. The composition of claim 1, wherein the AHA comprises about 1-30% of the composition.

4. The composition of claim 1, wherein the AHA comprises about 1-10% of the composition.

5. The composition of claim 1 wherein the otologically acceptable vehicle further includes sodium docusate.

6. The composition of claim 1, wherein the composition is a topical composition administered to the ear canal.

7. A method for removing cerumen from a patient in need thereof comprising:
   administering to a patient in need thereof a composition comprising an AHA and an otologically acceptable vehicle, wherein the otologically acceptable vehicle is a sodium or potassium salts of bicarbonate aqueous buffer.

8. The method of claim 7, wherein the composition is administered topically.

9. The method of claim 7, wherein the composition remains in contact with the cerumen for about 15-30 minutes prior to removal.

10. The method of claim 7, wherein the composition is applied and removed at least once.

11. The method of claim 7, wherein the composition results in about 65% change in cerumen.

12. A method of treating a cerumen impaction comprising:
   administering topically to a patient's ear in need thereof a composition having an AHA and an otologically acceptable vehicle, wherein the otologically acceptable vehicle is a sodium or potassium salts of bicarbonate aqueous buffer.

13. The method of claim 12, wherein the composition improves cerumen impaction comprising full occlusion, crescent shape, or ring shape by alleviating at least one or more blockage symptoms selected from the group consisting of:
   hearing loss, fullness feeling, ear ringing, ear itching, water trapping, ear pain, ear irritation or a combination thereof.

14. The method of claim 12, wherein the composition is administered unilaterally or bilaterally.

15. The method of claim 12, wherein the composition reduces cerumen impaction to less than about 3%.

16. The method of claim 12, wherein the composition reduces cerumen impaction from about 76-100% to at least about 3-75%.

17. The method of claim 12, wherein the composition reduces cerumen impaction to from about 51-75% to at least about 3-50%.

18. The method of claim 12, wherein the composition reduces cerumen impaction from about 26-50% to at least about 3-35%.

* * * * *